United States Patent
Skoczen et al.

(10) Patent No.: US 11,013,693 B2
(45) Date of Patent: *May 25, 2021

(54) PROCESS FOR PREPARATION OF AN ENTERIC COATED GRANULATE COMPRISING DIMETHYL FUMARATE

(71) Applicant: Zaklady Farmaceutyczne Polpharma S.A., Starogard Gdanski (PL)

(72) Inventors: Przemyslaw Skoczen, Straszyn (PL); Aleksandra Drozd, Chrzastawa Mala (PL); Marek Cichocki, Cracow (PL)

(73) Assignee: Zaklady Farmaceutyczne Polpharma S.A.

( * ) Notice: Subject to any disclaimer, the term of this patent is extended or adjusted under 35 U.S.C. 154(b) by 135 days.

This patent is subject to a terminal disclaimer.

(21) Appl. No.: 16/067,335

(22) PCT Filed: Dec. 23, 2016

(86) PCT No.: PCT/EP2016/002175
§ 371 (c)(1),
(2) Date: Jun. 29, 2018

(87) PCT Pub. No.: WO2017/114593
PCT Pub. Date: Jul. 6, 2017

(65) Prior Publication Data
US 2020/0163887 A1 May 28, 2020

(30) Foreign Application Priority Data

Dec. 31, 2015 (EP) .................................. 15460146

(51) Int. Cl.
*A61K 9/16* (2006.01)
*A61K 9/50* (2006.01)
*A61K 31/225* (2006.01)

(52) U.S. Cl.
CPC .......... *A61K 9/1694* (2013.01); *A61K 9/1611* (2013.01); *A61K 9/1652* (2013.01); *A61K 9/5073* (2013.01); *A61K 31/225* (2013.01)

(58) Field of Classification Search
CPC .. A61K 9/1611; A61K 9/1694; A61K 9/5073; A61K 9/1652; A61K 31/225
See application file for complete search history.

(56) References Cited

U.S. PATENT DOCUMENTS 8,906,420 B2 * 12/2014 Nilsson ................ A61K 9/2886
424/490
2014/0284245 A1   9/2014 Karabomi Sami et al.

FOREIGN PATENT DOCUMENTS

| CN | 104352441 | * 10/2014 |
| CN | 104288774 A | 1/2015 |
| EP | 2564839 A2 | 3/2013 |
| WO | WO 2007/042034 A1 | 4/2007 |
| WO | 2013076216 A1 | 5/2013 |
| WO | WO 2013/119677 | 8/2013 |
| WO | WO 2015/086467 A1 | 6/2015 |

* cited by examiner

*Primary Examiner* — Shirley V Gembeh
(74) *Attorney, Agent, or Firm* — William D. Hare, Esq.; McNeely, Hare & War, LLP

(57) ABSTRACT

The present invention relates to a process for the preparation of an oral pharmaceutical preparation in the form of enteric coated granulate comprising dimethyl fumarate and pharmaceutically acceptable excipients. The invention relates also to an oral pharmaceutical preparation in the form of enteric coated granulate obtained by the process of the present invention and to use of the preparation in the treatment of multiple sclerosis.

20 Claims, No Drawings

PROCESS FOR PREPARATION OF AN ENTERIC COATED GRANULATE COMPRISING DIMETHYL FUMARATE

The present invention relates to a process for the preparation of an oral pharmaceutical preparation in the form of enteric coated granulate comprising dimethyl fumarate and pharmaceutically acceptable excipients. The invention relates also to an oral pharmaceutical preparation in the form of enteric coated granulate obtained by the process of the present invention and to use of the preparation in the treatment of multiple sclerosis.

Multiple sclerosis is an autoimmune disease with the autoimmune activity directed against central nervous system antigens. The disease is characterized by inflammation in parts of the central nervous system, leading to the loss of the myelin, sheathing around neuronal axons (demyelination), axonal loss and the eventual death of neurons, oligodendrocytes and glial cells.

Dimethyl fumarate is used in the treatment of multiple sclerosis. A product in the form of encapsulated enteric coated mini-tablets comprising dimethyl fumarate as the sole active ingredient indicated for the treatment of relapsing remitting multiple sclerosis is marketed by Biogen Idec Ltd. under trade name Tecfidera®.

Pharmaceutical compositions comprising dimethyl fumarate are disclosed for example in EP1131065. EP1131065 discloses enteric coated pellets and mini-tablets comprising dimethyl fumarate as the sole active ingredient.

EP2564839 discloses a pharmaceutical formulation comprising an erodible matrix, wherein one or more fumaric acid esters and rate-controlling agents are located within the matrix. The erosion of the matrix permitting controlled or sustained release of the fumaric acid esters.

WO2007042034 also discloses a controlled release formulation comprising fumaric acid esters, wherein the composition comprises di and/or monoalkyl esters of fumaric acid and 8-15% by weight of a pharmaceutically acceptable polymer.

In case of enteric coated preparations, regularity of shape of the uncoated preparation is considered to play a significant role since it allows for applying a uniform layer of enteric coating. Irregular shape of the core of the preparation is considered to cause differences in the coating thickness, which leads to reduction of protection offered by the enteric coating to the preparation in lower pH conditions.

Surprisingly, it was found that a pharmaceutical preparation in the form of an enteric coated granulate comprising dimethyl fumarate and pharmaceutically acceptable excipients can be obtained by dry granulation. The enteric coated granulate obtained by the process of the present invention offers suitable protection from release of the drug substance in lower pH conditions and rapid release in pH conditions of the intestine.

The invention relates to a process for the manufacture of an oral pharmaceutical preparation in the form of enteric coated granulate comprising dimethyl fumarate, which comprises the following steps:
a) blending dimethyl fumarate with pharmaceutically acceptable excipients comprising a disintegrant, an adsorbent, a lubricant and, optionally, a binder and/or filler;
b) dry granulating the blend obtained in step a) to obtain a granulate;
c) coating the granulate obtained in step b) with one or more layers of enteric coating.

In a preferred embodiment of the invention, dimethyl fumarate is present in the blend obtained in step a) in the amount from 65 to 95% by weight with respect to the total weight of the blend.

In another preferred embodiment of the invention, the disintegrant is present in the blend obtained in step a) in the amount from 4 to 12% by weight with respect to the total weight of the blend.

In another preferred embodiment of the invention, dimethyl fumarate is present in the blend obtained in step a) in the amount from 65 to 95% by weight with respect to the total weight of the blend, and the disintegrant is present in the blend obtained in step a) in the amount from 4 to 12% by weight with respect to the total weight of the blend.

In yet another preferred embodiment of the invention, the disintegrant is selected from croscarmellose sodium, sodium starch glycolate, crospovidone, low-substituted hydroxypropyl cellulose and mixtures thereof.

In another preferred embodiment of the invention, the disintegrant is present in the blend obtained in step a) in the amount from 4 to 12% by weight with respect to the total weight of the blend and the disintegrant is selected from croscarmellose sodium, sodium starch glycolate, crospovidone, low-substituted hydroxypropyl cellulose and mixtures thereof.

Dimethyl fumarate readily undergoes hydrolysis. The role of an adsorbent is to protect dimethyl fumarate from moisture present in the enteric coated preparation before the product is administered to a patient. Hence, enteric coated granulate manufactured according to the process of the present invention offers increased chemical stability of dimethyl fumarate. A further role of adsorbent is to increase water uptake of the granulate thus improving the performance of disintegrant resulting in promotion of release of dimethyl fumarate upon dissolving of the enteric coating of the granulate in the intestine.

In a preferred embodiment of the invention, the adsorbent is present in the blend obtained in step a) in the amount from 0.5 to 10% by weight with respect to the total weight of the blend.

In another preferred embodiment of the invention, the adsorbent is selected from silicon dioxide, aluminum magnesium silicate and mixtures thereof. The preferred adsorbent is silicon dioxide.

In another preferred embodiment of the invention the adsorbent is present in the blend obtained in step a) in the amount from 0.5 to 10% by weight with respect to the total weight of the blend and the adsorbent is selected from silicon dioxide, aluminum magnesium silicate and mixtures thereof. The preferred adsorbent is silicon dioxide.

In yet another preferred embodiment of the invention, the lubricant is present in the blend obtained in step a) in the amount from 0.5 to 2% by weight with respect to the total weight of the blend.

In another preferred embodiment of the invention, the lubricant is selected from magnesium stearate, calcium stearate, stearic acid, sodium stearyl fumarate, glyceryl behenate, glyceryl palmitostearate and mixtures thereof.

In another preferred embodiment of the invention the lubricant is present in the blend obtained in step a) in the amount from 0.5 to 2% by weight with respect to the total weight of the blend and the lubricant is selected from magnesium stearate, calcium stearate, stearic acid, sodium stearyl fumarate, glyceryl behenate, glyceryl palmitostearate and mixtures thereof.

In another preferred embodiment of the invention, the disintegrant is present in the blend obtained in step a) in the amount from 4 to 12% by weight with respect to the total weight of the blend and the adsorbent is present in the blend obtained in step a) in the amount from 0.5 to 10% by weight with respect to the total weight of the blend and the lubricant is present in the blend obtained in step a) in the amount from 0.5 to 2% by weight with respect to the total weight of the blend.

In a preferred embodiment of the invention, the binder and/or filler is present in the blend obtained in step a) in the amount up to 20% by weight with respect to the total weight of the blend.

In another preferred embodiment of the invention, the binder and/or filler is preferably selected from microcrystalline cellulose, mannitol, anhydrous dibasic calcium phosphate and mixtures thereof. It should be noted that some of binders and fillers can be used interchangeably as they exhibit both properties.

The process of granulation defined in step b) is preferably performed using roller compaction technique.

In yet another preferred embodiment of the invention, the enteric coated granulate obtained in step c) is further coated by applying a suspension comprising silicon dioxide, preferably using fluid bed coating method.

In another preferred embodiment of the invention, the process of coating with a suspension of silicon dioxide is performed using aqueous suspension comprising silicon dioxide. Silicon dioxide is preferably the sole solid ingredient forming the suspension.

Another aspect of the invention relates to an oral pharmaceutical preparation in the form enteric coated granulate obtained by the process as defined above.

In a preferred embodiment of the invention, the preparation has three coating layers with two inner enteric coating layers comprising different enteric film-forming polymers and an outer coating formed by fluid bed coating with a suspension comprising silicon dioxide. Silicon dioxide is preferably the sole solid ingredient forming the suspension.

In another preferred embodiment of the invention, the preparation has four coating layers with three inner enteric coating layers comprising different enteric film-forming polymers and an outer coating formed by fluid bed coating with a suspension comprising silicon dioxide. Silicon dioxide is preferably the sole solid ingredient forming the suspension.

In a preferred embodiment of the invention, the enteric coated preparation of the present invention is filled into capsules or sachets.

A further aspect of the invention relates to an oral pharmaceutical preparation in the form enteric coated granulate obtained by the process as defined above for use in the treatment of multiple sclerosis.

The following non-limiting examples will further illustrate the invention. The skilled person would appreciate that amounts of components given in tables as a percentage [%] w/w and defining the composition of intermediate and final granulates are equivalent to the amounts of components used for manufacturing the relevant granulates.

EXAMPLES

Example 1

Dimethyl fumarate, croscarmellose sodium and silicon dioxide were sieved and blended. Then, sodium stearyl fumarate was sieved, added to the blend and mixed. The blend was subsequently granulated using roller compactor. Thus obtained granulate was filled into hard gelatin capsules affording the dose of 240 mg per capsule. The following composition was obtained:

| Ingredient | [%] w/w | mg/caps. |
|---|---|---|
| Dimethyl fumarate | 87.91 | 240.00 |
| Croscarmellose sodium | 8.96 | 24.47 |
| Sodium stearyl fumarate | 0.95 | 2.59 |
| Silicon dioxide | 2.18 | 5.94 |
| TOTAL | 100.00 | 273.00 |

Comparative Example 1

Dimethyl fumarate and croscarmellose sodium were sieved and blended. Then, sodium stearyl fumarate was sieved, added to the blend and mixed. Thus obtained blend was granulated using roller compactor. The resulting granulate was subsequently filled into hard gelatin capsules affording the dose of 240 mg per capsule. The following composition was obtained:

| Ingredient | % w/w | mg/caps. |
|---|---|---|
| Dimethyl fumarate | 91.60 | 240.00 |
| Croscarmellose sodium | 7.00 | 18.40 |
| Sodium stearyl fumarate | 1.40 | 3.60 |
| TOTAL | 100.00 | 262.00 |

Comparative Example 2

Dimethyl fumarate and croscarmellose sodium were sieved and blended. Then, sodium stearyl fumarate was sieved, added to the blend and mixed. Thus obtained blend was granulated using roller compactor. The resulting granulate was subsequently filled into hard gelatin capsules affording the dose of 240 mg per capsule. The following composition was obtained:

| Ingredient | % w/w | mg/caps. |
|---|---|---|
| Dimethyl fumarate | 88.89 | 240.00 |
| Croscarmellose sodium | 9.70 | 26.20 |
| Sodium stearyl fumarate | 1.41 | 3.80 |
| TOTAL | 100.00 | 270.00 |

Comparison of Dissolution

Granulates of Example 1, Comparative Example 1 and Comparative Example 2 were filled into hard gelatin capsules affording the dose of 240 mg per capsule and tested for dissolution in phosphate buffer (pH 6.8) without any pretreatment in a solution of hydrochloric acid. The following results were achieved:

| | Dissolution in phosphate buffer (pH 6.8) [%] | | | | | | |
|---|---|---|---|---|---|---|---|
| Tested product | 5 min. | 10 min. | 15 min. | 20 min. | 30 min. | 45 min. | 60 min. |
| Capsule of Ex. 1 | 70.0 | 97.1 | 101.5 | 103.9 | 102.4 | 101.7 | 101.2 |
| Capsule of Comparative Ex. 1 | 1.2 | 10.6 | 24.6 | 38.2 | 58.1 | 75.7 | 85.2 |

| Tested product | Dissolution in phosphate buffer (pH 6.8) [%] | | | | | | |
|---|---|---|---|---|---|---|---|
| | 5 min. | 10 min. | 15 min. | 20 min. | 30 min. | 45 min. | 60 min. |
| Capsule of Comparative Ex. 2 | 2.6 | 17.8 | 40.0 | 59.9 | 78.1 | 88.4 | 93.2 |

It was observed that the encapsulated granulate of Example 1 achieved much faster dissolution of dimethyl fumarate in the phosphate buffer (pH 6.8) as compared to capsules of Comparative Example 1 and Comparative Example 2. This difference may not be awarded to the presence of disintegrant in the product as the amount of croscarmellose sodium in the granulate of Comparative Example 2 is higher when compared to the granulate of Example 1. Hence, it may be concluded that the presence of an adsorbent in the preparation obtained by the process of the present invention promotes release of dimethyl fumarate upon dissolving of enteric coating of the granulate.

Example 2

The granulate obtained in Example 1 was fluid bed coated using a suspension of enteric film-forming polymer methacrylic acid-methyl methacrylate copolymer in the ratio of 1:1 by weight (commercially available from Evonik as Eudragit L12.5), talc and triethyl citrate in isopropanol.

The enteric coated granulate was then fluid bed coated using aqueous suspension of enteric film-forming polymer methacrylic acid-ethyl acrylate copolymer in the ratio of 1:1 by weight (commercially available from Evonik as Eudragit L30 D-55) and a mixture of triethyl citrate, glycerol monostearate, polysorbate 80.

Thus obtained enteric coated granulate was filled into hard gelatin capsules affording the dose of 240 mg per capsule. The following composition was obtained:

| Ingredient | % w/w | mg/caps. |
|---|---|---|
| Core | | |
| Dimethyl fumarate | 48.00 | 240.00 |
| Croscarmellose sodium | 4.89 | 24.47 |
| Sodium stearyl fumarate | 0.52 | 2.59 |
| Silicon dioxide | 1.19 | 5.94 |
| 1$^{st}$ coating layer | | |
| Methacrylic acid-methyl methacrylate copolymer (1:1) | 6.86 | 34.30 |
| Talc | 3.40 | 17.01 |
| Triethyl citrate | 0.66 | 3.29 |
| 2$^{nd}$ coating layer | | |
| Methacrylic acid-ethyl acrylate copolymer (1:1) | 29.47 | 147.33 |
| Triethyl citrate | 2.96 | 14.78 |
| Glycerol monostearate | 1.47 | 7.35 |
| Polysorbate 80 | 0.58 | 2.94 |
| TOTAL | 100.00 | 500.00 |

Example 3

The granulate obtained in Example 2 was subsequently fluid bed coated using an aqueous suspension of silicon dioxide. Thus obtained enteric coated granulate with an outer silicon dioxide coating was filled into hard gelatin capsules affording the dose of 240 mg per capsule. The following composition was obtained:

| Ingredient | % w/w | mg/caps. |
|---|---|---|
| Core | | |
| Dimethyl fumarate | 47.52 | 240.00 |
| Croscarmellose sodium | 4.85 | 24.47 |
| Sodium stearyl fumarate | 0.51 | 2.59 |
| Silicon dioxide | 1.18 | 5.94 |
| 1$^{st}$ coating layer | | |
| Methacrylic acid-methyl methacrylate copolymer (1:1) | 6.80 | 34.30 |
| Talc | 3.37 | 17.01 |
| Triethyl citrate | 0.65 | 3.29 |
| 2$^{nd}$ coating layer | | |
| Methacrylic acid-ethyl acrylate copolymer (1:1) | 29.17 | 147.33 |
| Triethyl citrate | 2.93 | 14.78 |
| Glycerol monostearate | 1.46 | 7.35 |
| Polysorbate 80 | 0.57 | 2.94 |
| 3$^{rd}$ coating layer | | |
| Silicon dioxide | 0.99 | 5.00 |
| TOTAL | 100.00 | 505.00 |

Testing of Dissolution

A hard gelatin capsule with enteric coated granulate of Example 3 was tested for dissolution in phosphate buffer (pH 6.8) after treating for 2 hours in 0.1M solution of hydrochloric acid. The following results were obtained:

| Tested product | Dissolution in 0.1M HCl [%] | Dissolution in phosphate buffer (pH 6.8) [%] | | | | | | |
|---|---|---|---|---|---|---|---|---|
| | 120 min. | 5 min. | 10 min. | 15 min. | 20 min. | 30 min. | 45 min. | 60 min. |
| Capsule of Ex. 3 | 1.5 | 12.9 | 65.2 | 96.8 | 101.7 | 102.7 | 102.0 | 101.6 |

It was observed that the encapsulated enteric coated granulate of Example 3 achieved minimal dissolution in acidic media, i.e. in 0.1M solution of hydrochloric acid, while complete dissolution of dimethyl fumarate in the phosphate buffer (pH 6.8) was reached in less than 20 minutes. Hence, it may be concluded that the process of the present invention provides an enteric coated granulate with sufficient protection from release of the drug substance in lower pH conditions and rapid release in pH conditions of the intestine.

The invention claimed is:

1. Process for the manufacture of an oral pharmaceutical preparation in the form of enteric coated granulate comprising dimethyl fumarate, which comprises the following steps:
   a) blending dimethyl fumarate with pharmaceutically acceptable excipients comprising a disintegrant, an adsorbent, a lubricant and, optionally, a binder and/or filler;
   b) dry granulating the blend obtained in step a) to obtain a granulate; and
   c) coating the granulate obtained in step b) with one or more layers of enteric coating.

2. Process according to claim 1, wherein dimethyl fumarate is present in the blend obtained in step a) in the amount from 65 to 95% by weight with respect to the total weight of the blend.

3. Process according to claim 1, wherein the disintegrant is present in the blend obtained in step a) in the amount from 4 to 12% by weight with respect to the total weight of the blend.

4. Process according to claim 1, wherein the disintegrant is selected from croscarmellose sodium, sodium starch glycolate, crospovidone, low-substituted hydroxypropyl cellulose and mixtures thereof.

5. Process according to claim 1, wherein the adsorbent is present in the blend obtained in step a) in the amount from 0.5 to 10% by weight with respect to the total weight of the blend.

6. Process according to claim 1, wherein the adsorbent is selected from silicon dioxide, aluminum magnesium silicate and mixtures thereof.

7. Process according to claim 1, wherein the lubricant is present in the blend obtained in step a) in the amount from 0.5 to 2% by weight with respect to the total weight of the blend.

8. Process according to claim 1, wherein the lubricant is selected from magnesium stearate, calcium stearate, stearic acid, sodium stearyl fumarate, glyceryl behenate, glyceryl palmitostearate and mixtures thereof.

9. Process according to claim 1, wherein the binder and/or filler is present in the blend obtained in step a) in the amount up to 20% by weight with respect to the total weight of the blend.

10. Process according to claim 1, wherein the binder and/or filler is selected from microcrystalline cellulose, mannitol, anhydrous dibasic calcium phosphate and mixtures thereof.

11. Process according to claim 1, wherein the enteric coated granulate obtained in step c) is further coated with a suspension comprising silicon dioxide.

12. Process according to claim 11, wherein the suspension comprising silicon dioxide is applied using a fluid bed coating method.

13. Process according to claim 11, wherein the suspension of silicon dioxide is an aqueous suspension.

14. The process according to claim 13, wherein the suspension of silicon dioxide is an aqueous suspension consisting of the silicon dioxide and water.

15. An oral pharmaceutical preparation in the form enteric coated granulate obtained by the process according to claim 1.

16. A method of treating multiple sclerosis, the method comprising administering the oral pharmaceutical preparation according to claim 15.

17. The oral pharmaceutical preparation according to claim 15, wherein the preparation is filled into capsules or sachets.

18. A process for the manufacture of an oral pharmaceutical preparation in the form of enteric coated granulate comprising dimethyl fumarate, the process consisting of the steps of:
   a) blending dimethyl fumarate with pharmaceutically acceptable excipients comprising a disintegrant, an adsorbent, a lubricant and, optionally, a binder and/or filler;
   b) dry granulating the blend obtained in step a) to obtain a granulate;
   c) coating the granulate obtained in step b) with one or more layers of enteric coating; and
   d) coating the enteric coated granulate of step c) with a suspension of silicon dioxide.

19. The process according to claim 18, wherein
   the dimethyl fumarate is present in the blend obtained in step a) in an amount from 65 to 95% by weight with respect to the total weight of the blend;
   the disintegrant is present in the blend obtained in step a) in an amount from 4 to 12% by weight with respect to the total weight of the blend;
   the adsorbent is present in the blend obtained in step a) in an amount from 0.5 to 10% by weight with respect to the total weight of the blend;
   the lubricant is present in the blend obtained in step a) in an amount from 0.5 to 2% by weight with respect to the total weight of the blend; and
   the binder and/or filler is present in the blend obtained in step a) in an amount up to 20% by weight with respect to the total weight of the blend.

20. The process according to claim 18, wherein the silicon dioxide of the silicon dioxide coated granulates of step d) comprises 0.99% by weight of the total weight of the coated granules.

* * * * *